(12) United States Patent
Grunewald

(10) Patent No.: US 9,433,464 B2
(45) Date of Patent: Sep. 6, 2016

(54) CATHETER WITH NEEDLES FOR ABLATING TISSUE LAYERS IN VESSEL

(71) Applicant: Biosense Webster (Israel), Ltd., Yokneam (IL)

(72) Inventor: Debby Grunewald, Los Angeles, CA (US)

(73) Assignee: Biosense Webster (Israel) Ltd., Yokneam (IL)

(*) Notice: Subject to any disclaimer, the term of this patent is extended or adjusted under 35 U.S.C. 154(b) by 545 days.

(21) Appl. No.: 13/829,178

(22) Filed: Mar. 14, 2013

(65) Prior Publication Data

US 2014/0276779 A1    Sep. 18, 2014

(51) Int. Cl.
*A61B 18/14* (2006.01)
*A61B 18/00* (2006.01)

(52) U.S. Cl.
CPC .. *A61B 18/1492* (2013.01); *A61B 2018/00404* (2013.01); *A61B 2018/00434* (2013.01); *A61B 2018/00511* (2013.01); *A61B 2018/1467* (2013.01)

(58) Field of Classification Search
CPC .................................................. A61B 18/1492
See application file for complete search history.

(56) References Cited

U.S. PATENT DOCUMENTS

| 4,391,199 | A | 7/1983 | Morin |
|---|---|---|---|
| 6,016,452 | A | 1/2000 | Kasevich |
| 6,156,033 | A | 12/2000 | Tu et al. |
| 6,638,275 | B1 | 10/2003 | McGaffigan et al. |
| 7,617,005 | B2 | 11/2009 | Demarais et al. |
| 7,935,082 | B2 | 5/2011 | Datta et al. |
| 8,048,066 | B2 | 11/2011 | Lafontaine |
| 8,152,803 | B2 | 4/2012 | Edwards et al. |
| 8,152,804 | B2 | 4/2012 | Elmouelhi et al. |
| 8,747,351 | B2 | 6/2014 | Schultz |
| 9,033,916 | B2 | 5/2015 | Schultz |
| 2002/0177864 | A1* | 11/2002 | Camrud ............... A61B 5/1411 606/167 |
| 2006/0224118 | A1* | 10/2006 | Morris .................. A61M 5/158 604/164.01 |
| 2010/0049031 | A1 | 2/2010 | Fruland et al. |
| 2010/0145265 | A1* | 6/2010 | Min .................. A61M 25/0068 604/95.03 |
| 2011/0054466 | A1 | 3/2011 | Rothstein et al. |

(Continued)

FOREIGN PATENT DOCUMENTS

WO    WO 02/087666 A2    11/2002
WO    WO 2012/058244 A2    5/2012

OTHER PUBLICATIONS

European Patent Office Communication dated Jul. 4, 2014 and Partial European Search Report dated Jun. 26, 2014 for EP Patent Application No. 14159589.2, 5 pgs.

*Primary Examiner* — Carl H Layno
*Assistant Examiner* — Jennifer Ghand
(74) *Attorney, Agent, or Firm* — Lewis Roca Rothgerber Christie LLP

(57) ABSTRACT

A catheter has a catheter body and a distal tip section with needles that are positioned radially to extend outside of the distal tip section to pierce and penetrate tissue layers of a vessel or tubular region. The needles are supported in a retracted position inside the distal tip section on an elongated support member. For deployment, the needles are lifted and a portion thereof pushed through openings in the distal tip section by an actuator that is longitudinally slidable on the elongated support member. The actuator has a tapered end to help lift the needle onto the actuator. In another embodiment, an inflatable balloon member with needles is movable between retracted and deployed positions.

13 Claims, 14 Drawing Sheets

(56) References Cited

U.S. PATENT DOCUMENTS

2011/0184385 A1* 7/2011 Datta ................ A61M 25/0136
                                                              604/528
2012/0184952 A1   7/2012 Jenson et al.

* cited by examiner

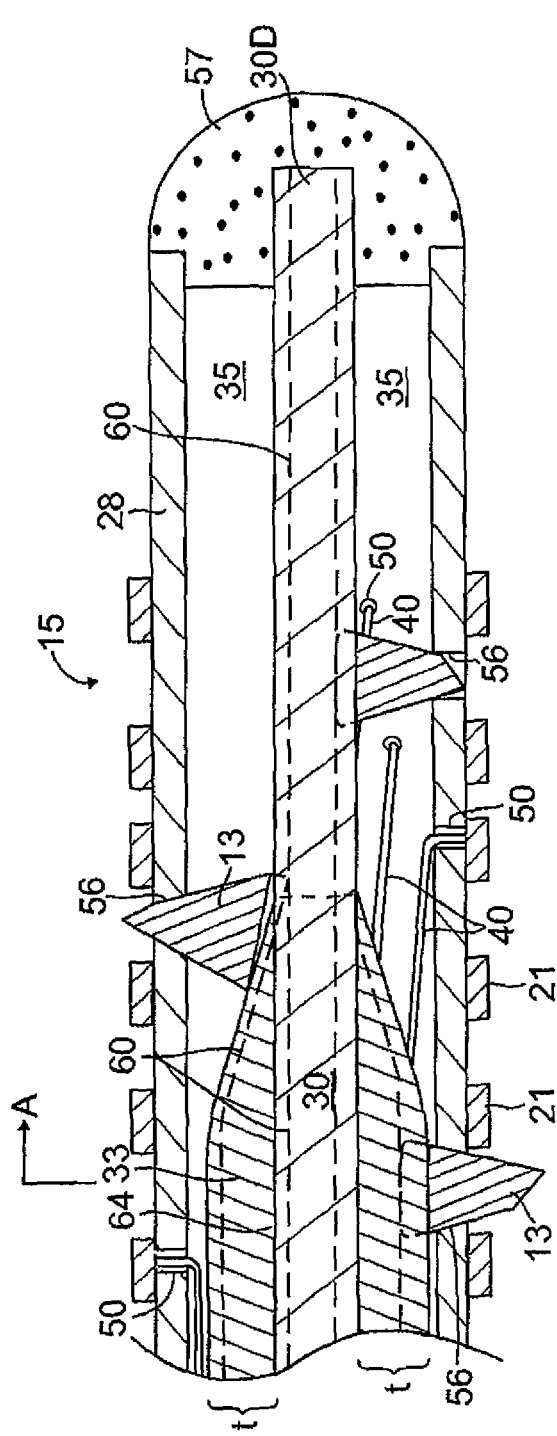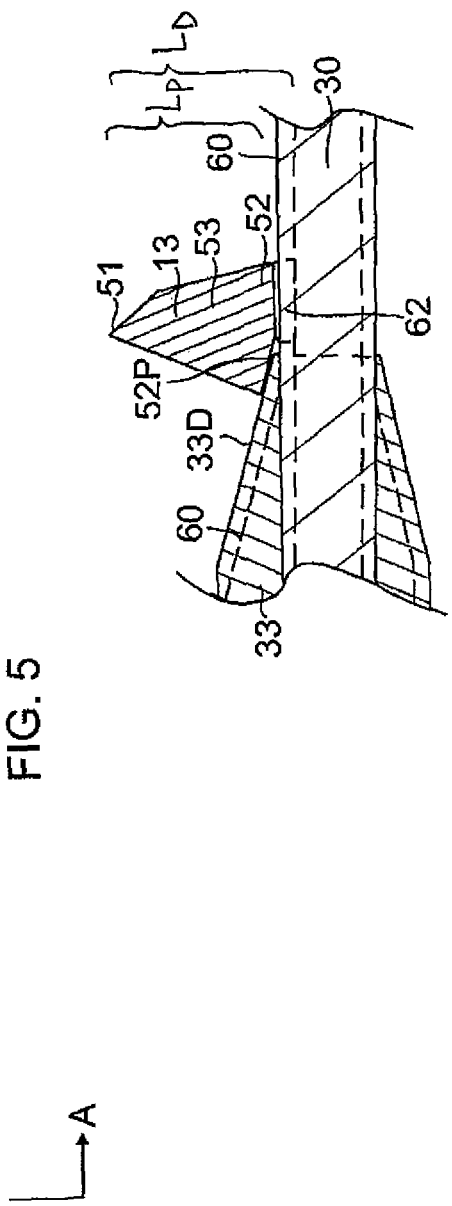
FIG. 5
FIG. 5B

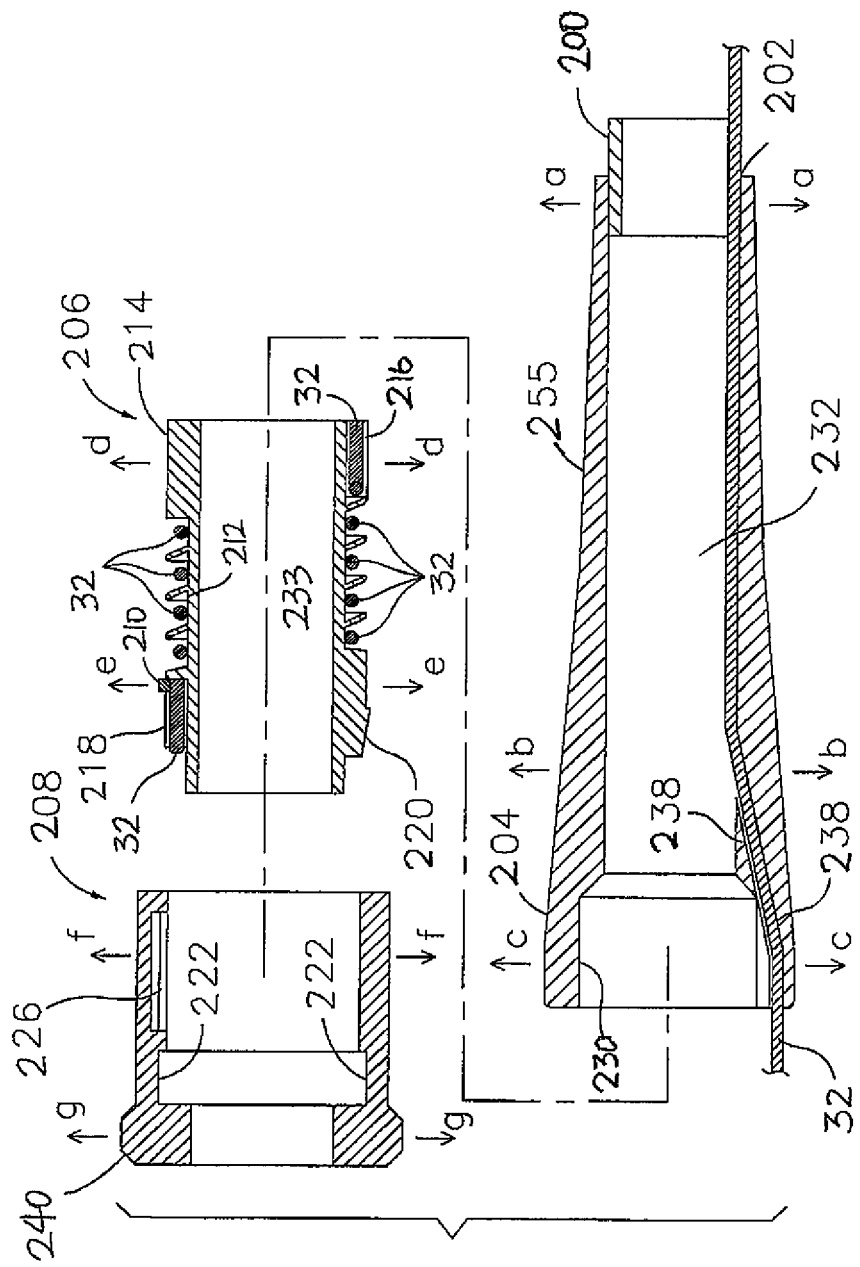

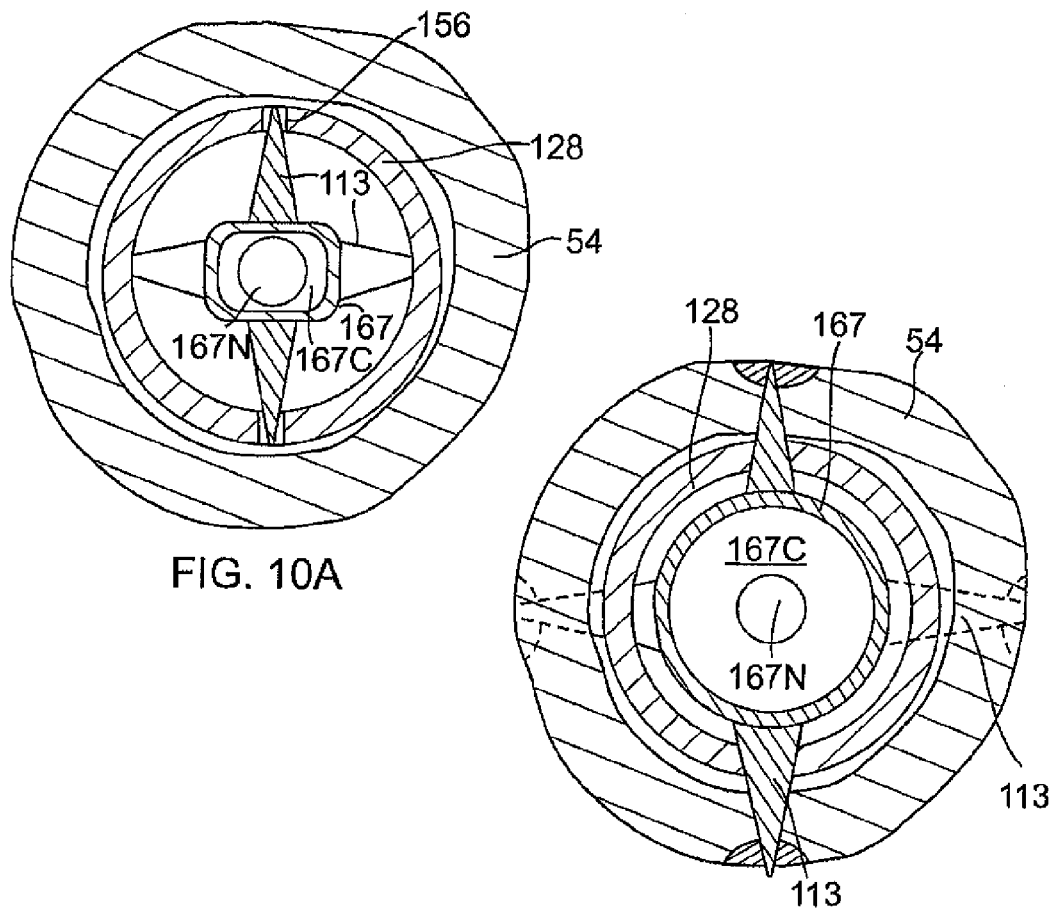
FIG. 10A
FIG. 11B
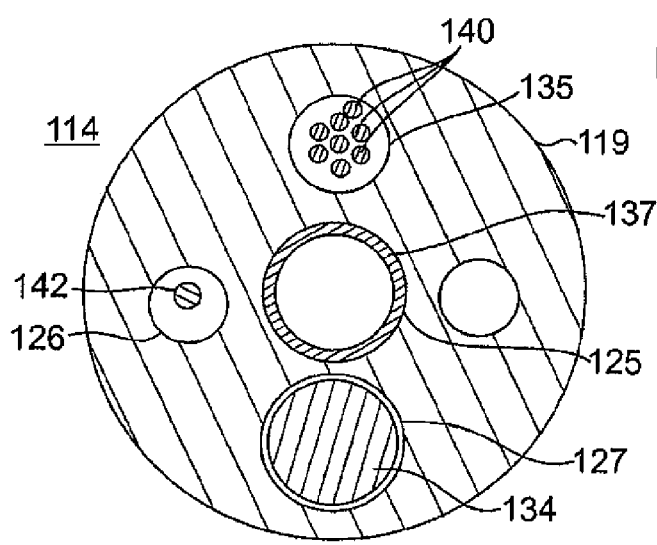
FIG. 11A

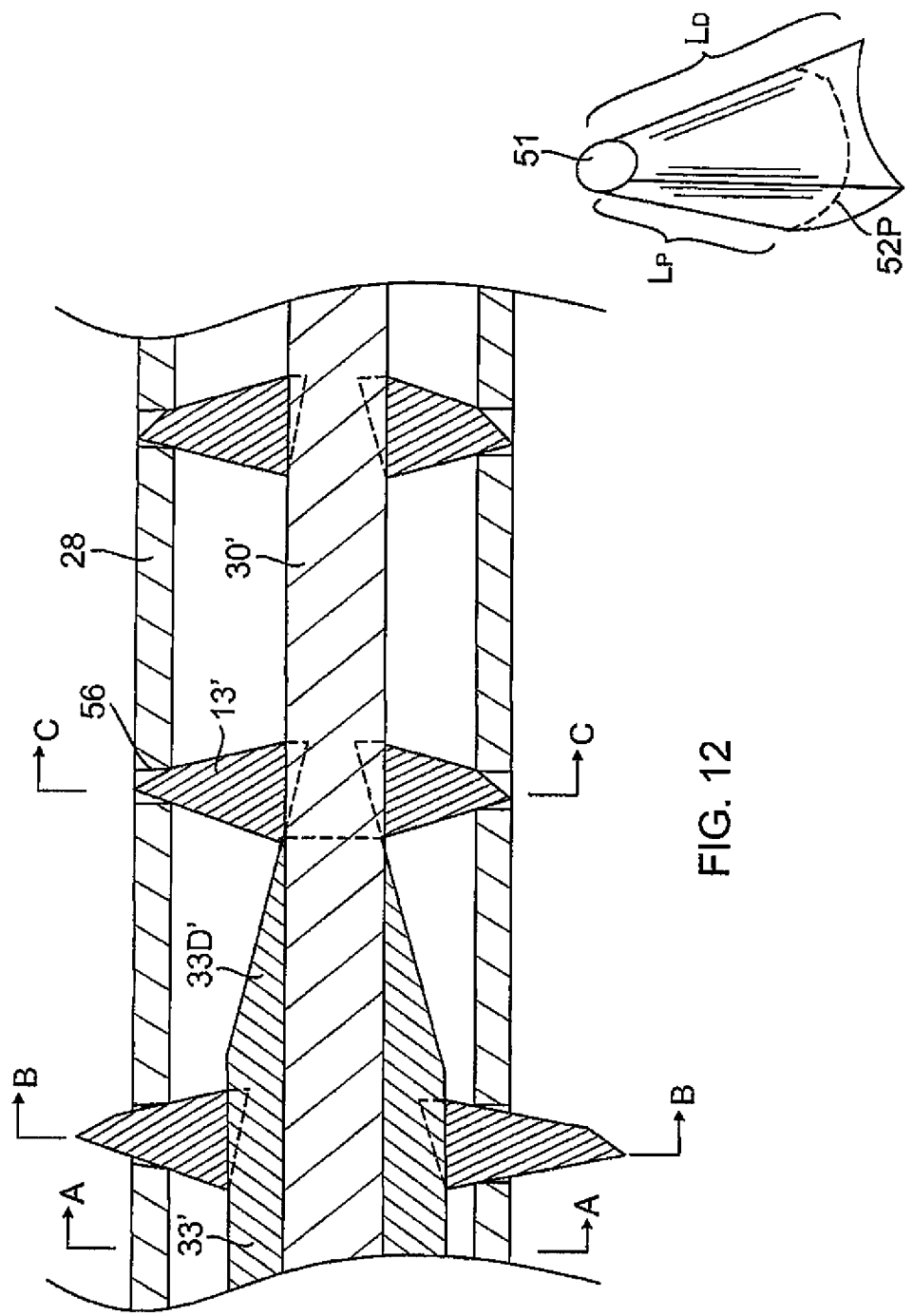

CATHETER WITH NEEDLES FOR ABLATING TISSUE LAYERS IN VESSEL

FIELD OF INVENTION

The present invention relates to catheters, in particular, catheters with a control handle and a lumened catheter body.

BACKGROUND OF INVENTION

Catheter-based procedures are on the rise. Many procedures that used to require major surgery can now be performed with minimal invasiveness by means of a catheter which can be inserted into the patient's body through a tiny incision no more than two to three inches long typically in the leg. Catheter-based procedures conducted on the heart may include balloon angioplasty, coronary angiogram, atherectomy, transmyocardial revascularization (TMR), percutaneous balloon valvoplasty, ablation and heart valve replacement A more recently developed catheterization procedure is renal denervation (RDN). It is a minimally invasive, endovascular catheter-based procedure using radiofrequency ablation aimed at treating resistant hypertension. Resistant hypertension is a common clinical problem faced by both primary care clinicians and specialists. As older age and obesity are two of the strongest risk factors for uncontrolled hypertension, the incidence of resistant hypertension will likely increase as the population becomes more elderly and heavier.

As one of the three major parts of the autonomic nervous system, the sympathetic system fuels the release of certain hormones that affect and control blood pressure. In hypertension, the continued release of low-dose amounts of these hormones can increase blood pressure. Hypertension can be controlled by diet, exercise and drugs. However, resistant hypertension (commonly defined as blood pressure that remains above goal in spite of concurrent use of three antihypertensive agents of different classes) requires more aggressive treatments, including surgery. It has been established that severing the renal nerves improves blood pressure. However, this procedure involves surgery and all its attendant risks, and may result in global sympathetic denervation below the chest.

Being able to de-nervate, or silence, only the renal nerves through a catheter-based system is a crucial development. A small catheter is placed in the femoral artery and access to the nerves is gained through the renal artery. By passing an energy source into the renal artery and transmitting a low-dose energy, radiofrequency ablation, through the catheter, inbound and exiting renal sympathetic nerves are impaired or "denerved" at selected locations along their lengths. This causes reduction of renal sympathetic afferent and efferent activity and blood pressure can be decreased. However, the renal nerves are embedded in the casings or layers around the renal arteries and may not be readily accessed by a catheter ablating from within the renal artery.

Accordingly, there is a desire for an ablation catheter that can penetrate inner layers of the renal artery to reach the nerves in the outer layers of the renal artery.

SUMMARY OF THE INVENTION

The present invention is directed to catheters, including ablation catheters and renal denervation catheters. In one embodiment, a catheter has a catheter body and a distal tip section with needles that are positioned radially to extend outside of the distal tip section to pierce and penetrate tissue layers of a vessel or tubular region. The needles are supported in a retracted position inside the distal tip section on an elongated support member that extends through at least the distal tip section. For deployment, the needles are lifted and a portion thereof pushed through openings in the distal tip section by an actuator that is longitudinally slidable on the elongated support member. The catheter includes a control handle by which an operator can manipulate a wire that is adapted to move the actuator longitudinally.

In a detailed embodiment, the actuator has a tapered end that is brought into engagement with each needle for deployment to facilitate the needle lifting off the elongated support member and sliding onto the actuator. The elongated support member and the actuator may have a longitudinal track in which each needle rides on to provide stability to the needles and guide their movement between the retracted and deployed positions.

In a detailed embodiment, the actuator is in a circumferentially surrounding relationship with the support member. The support member may have a distal portion with a 2-D or 3-D shape that is imparted to the distal tip section.

In a detailed embodiment, each needle has a distal treatment portion that is adapted to pierce and penetrate tissue layers. Portion(s) of the treatment portion may be masked to selectively avoid ablation of tissue that comes into contact with the masked portion. Each needle may also have an angled portion that facilitates engagement with the actuator.

In a detailed embodiment, each needle may be tethered to the actuator to ensure that the needles are retracted into the distal tip section before the distal tip section is repositioned or removed from the vessel.

In another embodiment of the present invention, a catheter has a catheter body and a distal tip section with an inflatable balloon member and needles affixed to an outer surface of the balloon member, wherein inflation of the balloon member pushes a treatment portion of the needle to outside the distal tip section for deployment via an opening in the distal tip section. The catheter also includes a control handle proximal of the catheter body and a fluid tubing adapted to pass fluid in and out of the balloon member. When the balloon member is deflated, the needles retract back into the distal tip section.

BRIEF DESCRIPTION OF THE DRAWINGS

These and other features and advantages of the present invention will be better understood by reference to the following detailed description when considered in conjunction with the accompanying drawings wherein:

FIG. 5 is a side cross-sectional view of the distal tip section of FIG. 4, with needles in a deployed position.

FIG. 5B is an enlarged view of the distal tip section of FIG. 5, showing engagement between a needle and a needle actuator, in accordance with one embodiment of the present invention.

FIG. 9 is a side cross-sectional view of a wire control mechanism and a barrel of the control handle.

FIG. 10A is an end cross-sectional view of the distal tip section of FIG. 10, taken along line A-A.

FIG. 11A is an end cross-sectional view of the distal tip section of FIG. 11, taken along line A-A.

FIG. 11B is an end cross-sectional view of the distal tip section of FIG. 11, taken along line A-A.

FIG. 12 is a side cross-sectional view of a distal tip section in accordance with another embodiment of the present invention.

FIG. 12D is a perspective view of a needle of FIG. 12.

DETAILED DESCRIPTION OF THE INVENTION

Figure 1:
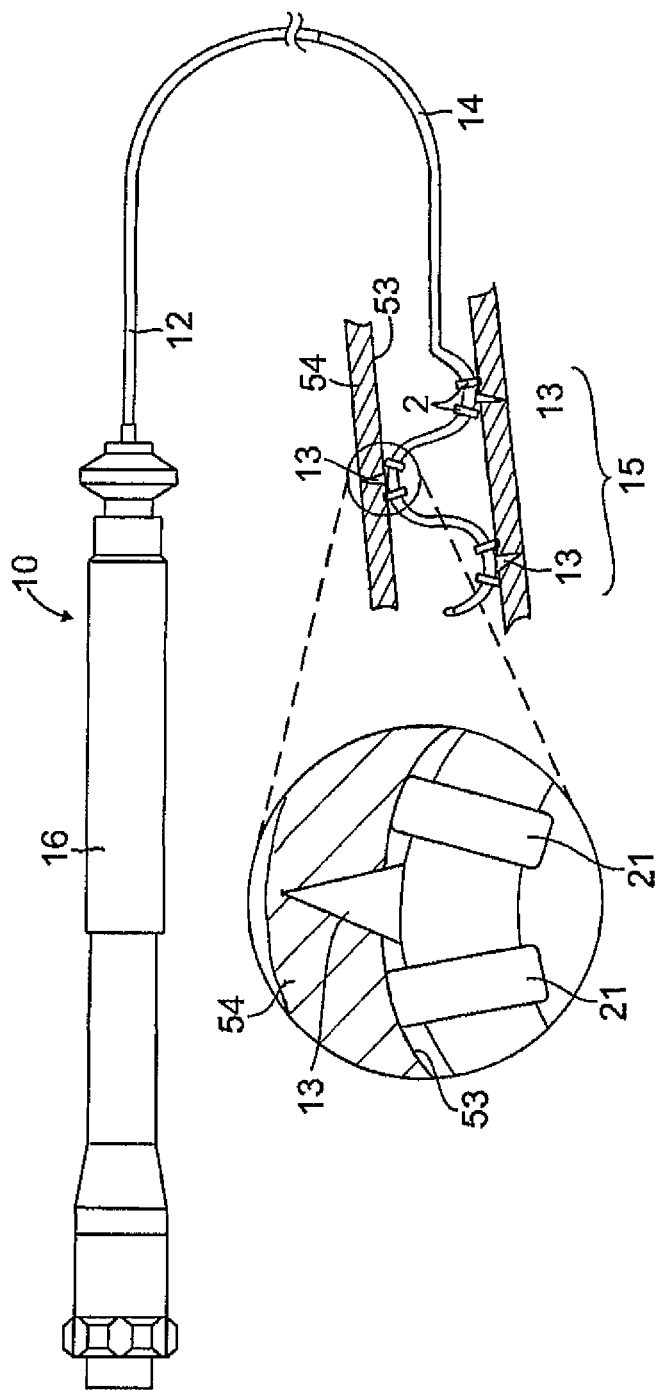
FIG. 1 is an elevated side view of a catheter, in accordance with an embodiment of the present invention.

With reference to FIG. 1, an ablation catheter 10 adapted to ablate a vessel while sparing or avoiding inner and middle layers if desired. The catheter 10 comprises an elongated catheter body 12, a distal tip section 15 at the distal end of the catheter body 12, and a control handle 16. The distal tip section 15 advantageously provides a plurality of individual needles (or injectors) 13 which are selectively extendable in a radial direction for ablating outermost tissue layer of a vessel 18, for example, a renal artery. The catheter 10 may also include an intermediate deflectable section 14 if desired.

Figure 2A:
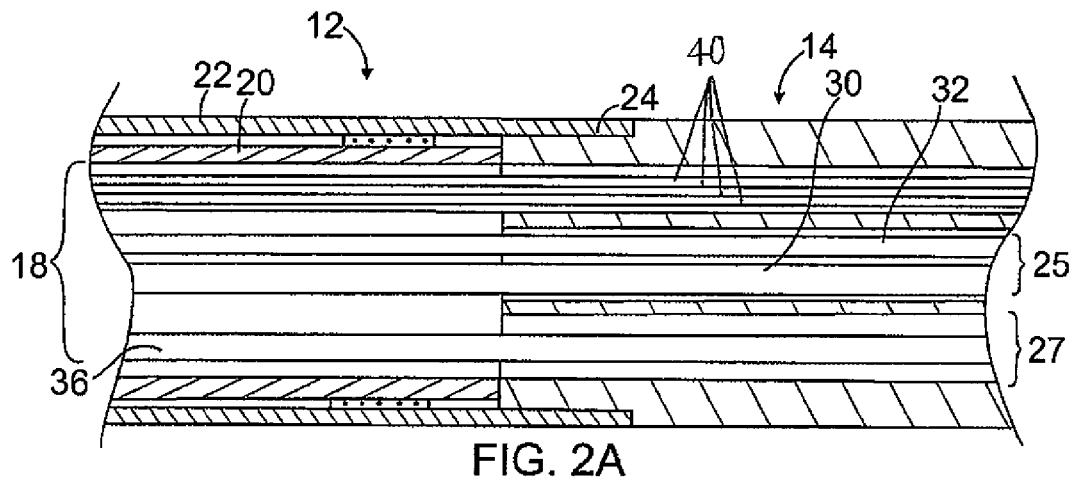
FIG. 2A is a side cross-sectional view of a catheter body, including the junction between the catheter body and an intermediate deflectable section, in accordance with an embodiment of the present invention, taken along a first diameter.
Figure 2B:
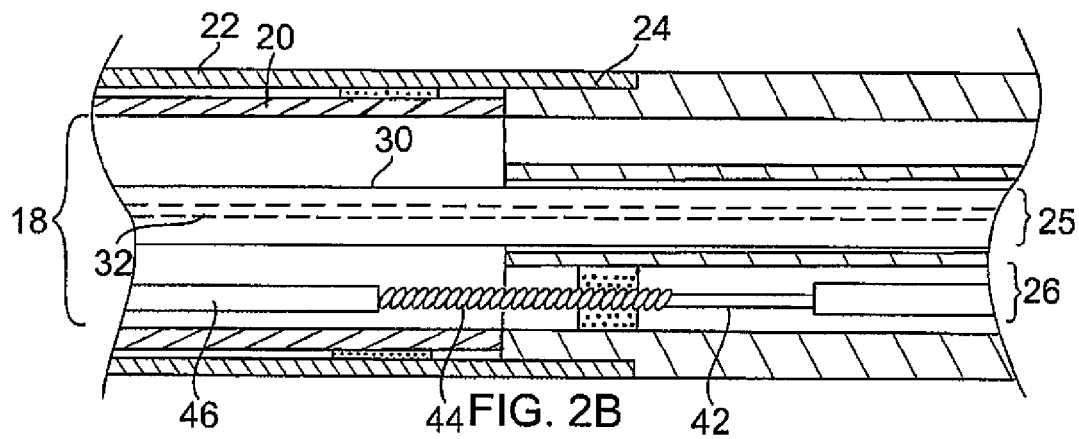
FIG. 2B is a side cross-sectional view of a catheter body, including the junction between the catheter body and an intermediate deflectable section, in accordance with an embodiment of the present invention, taken along a second diameter generally perpendicular to the first diameter.

With reference to FIGS. 2A and 2B, the catheter body 12 comprises an elongated tubular construction having a single, central or axial lumen 18. The catheter body 12 is flexible, i.e., bendable, but substantially non-compressible along its length. The catheter body 12 can be of any suitable construction and made of any suitable material. One construction comprises an outer wall 22 made of a polyurethane or PEBAX. The outer wall 22 comprises an imbedded braided mesh of stainless steel or the like to increase torsional stiffness of the catheter body 12 so that, when the control handle 16 is rotated, the tip section of the catheter 10 will rotate in a corresponding manner.

The outer diameter of the catheter body 12 is not critical. In one embodiment, the outer diameter is less than about 8 french, and more preferably about 6 french. Likewise the thickness of the outer wall 22 is not critical. The inner surface of the outer wall 22 is lined with a stiffening tube 20, which can be made of any suitable material, for example, polyimide. The stiffening tube, along with the braided outer wall 22, provides improved torsional stability while at the same time minimizing the wall thickness of the catheter, thus maximizing the diameter of the single lumen. The outer diameter of the stiffening tube 20 is about the same as or slightly smaller than the inner diameter of the outer wall 22. Polyimide tubing may be very thin walled while still providing very good stiffness. This maximizes the diameter of the central lumen 18 without sacrificing strength and stiffness. Polyimide material is typically not used for stiffening tubes because of its tendency to kink when bent. However, it has been found that, in combination with an outer wall 22 of polyurethane, PEBAX or other similar material, particularly having a stainless steel braided mesh, the tendency for the polyimide stiffening tube 20 to kink when bent is essentially eliminated with respect to the applications for which the catheter is used As shown in FIGS. 2A and 2B, various components extend through the single lumen 18 of the catheter body 12. These components includes a sensor cable 36 for an electromagnetic position sensor 34 (see FIG. 2C), a puller wire 42, a compression coil 44 for the puller wire, an elongated support member 30 and an advancing wire 32. A single lumen 18 catheter body compared to a multi-lumen body can permit better tip control when rotating the catheter 10. The single lumen 18 permits the components to float freely within the catheter body. If such components were restricted within multiple lumens, they can tend to build up energy when the handle 16 is rotated, resulting in the catheter body 12 having a tendency to rotate back if, for example, the handle is released, or if bent around a curve, to flip over, either of which are often undesirable performance characteristics.

FIGS. 2A and 2B illustrate a means for attaching the catheter body 12 to the deflectable section 14. The proximal end of the tip section 14 comprises an outer circumferential notch 24 that receives the inner surface of the outer wall 22 of the catheter body 12. The tip section 14 and catheter body 12 are attached by glue or the like. A spacer (not shown) may lie within the catheter body 12 between the distal end of the stiffening tube 20 and the proximal end of the tip section 14.

The spacer can be made of a material which is stiffer than the material of the tip section 14, e.g., polyurethane, but not as stiff as the material of the stiffening tube 20, e.g., polyimide. A spacer made of Teflon® may be used in one embodiment. The spacer may have an outer and inner diameter about the same as the outer and inner diameters of the stiffening tube 20. The spacer provides a transition in flexibility at the junction of the catheter body 12 and catheter tip 14, which allows the junction of the catheter body 12 and tip section 14 to bend smoothly without folding or kinking. The spacer is held in place by the stiffening tube 20. The stiffening tube 20, in turn, is held in place relative to the outer wall 22 by glue joints at the proximal end of the catheter body 12.

Figure 2C:
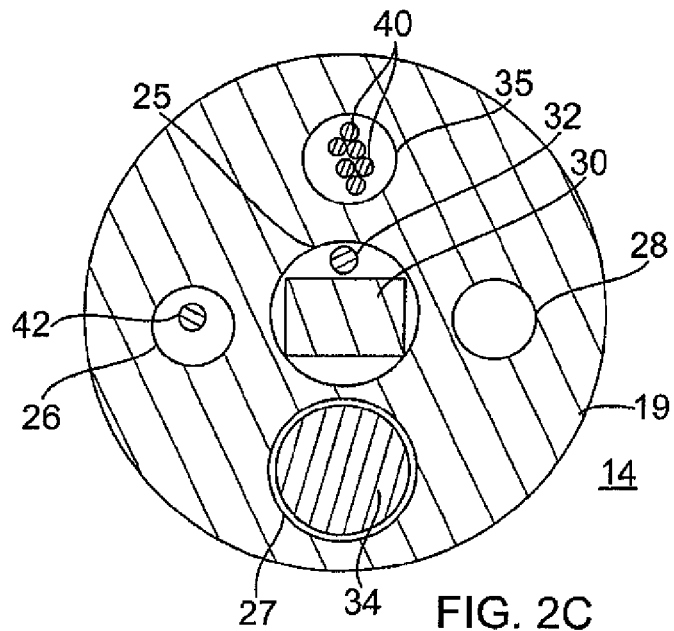
FIG. 2C is an end cross-section view of an intermediate deflectable section at or near its distal end, in accordance with an embodiment of the present invention.

As shown in FIGS. 2A, 2B and 2C, the deflectable section 14 comprises a shorter section of tubing 19 having a plurality of lumens, including lumens 25, 26 and 27. The tubing 19 is made of a suitable non-toxic material which can be more flexible than the catheter body 12. One material for the tubing 19 is braided polyurethane, i.e., polyurethane with an embedded mesh of braided stainless steel or the like. The outer diameter of the tip section 14, like that of the catheter body 12. The size of the lumens is not critical so long as they accommodate the component(s) extending therethrough.

It is understood that a single-lumened construction of the catheter body 12 may extend between the control handle 16 and the distal tip section 15 without a deflectable intermediate section 14 if deflection is not required of the catheter 10. Alternatively, a multi-lumened construction of the deflectable section 14 may extend between the control handle and the distal tip section 15 whether or not deflection is required of the catheter 10. That is, the aforementioned components may all extend through a single-lumened construction from the control handle 16 to the distal tip section 15 or they may extend through respective lumens of a multi-lumened construction from the control handle 16 to the distal tip section 15.

In the illustrated embodiment, the catheter 10 includes the catheter body 12 and the intermediate section 14, where the components extend through the central lumen 18 of the catheter body 12 and enter different lumens in the intermediate deflectable section 14. For example, the elongated support member 30 and the advancing wire 32 extend through center lumen 25. The puller wire 42 extends through off-axis lumen 26. (Where bi-directional deflection is desired, a second puller would extend through opposing off-axis lumen 28 as shown in FIG. 2C.) The sensor cable 36 extends through the lumen 27 with the position sensor 34 positioned in a distal end of the lumen 27 (as also shown in FIG. 2C).

Figure 3:
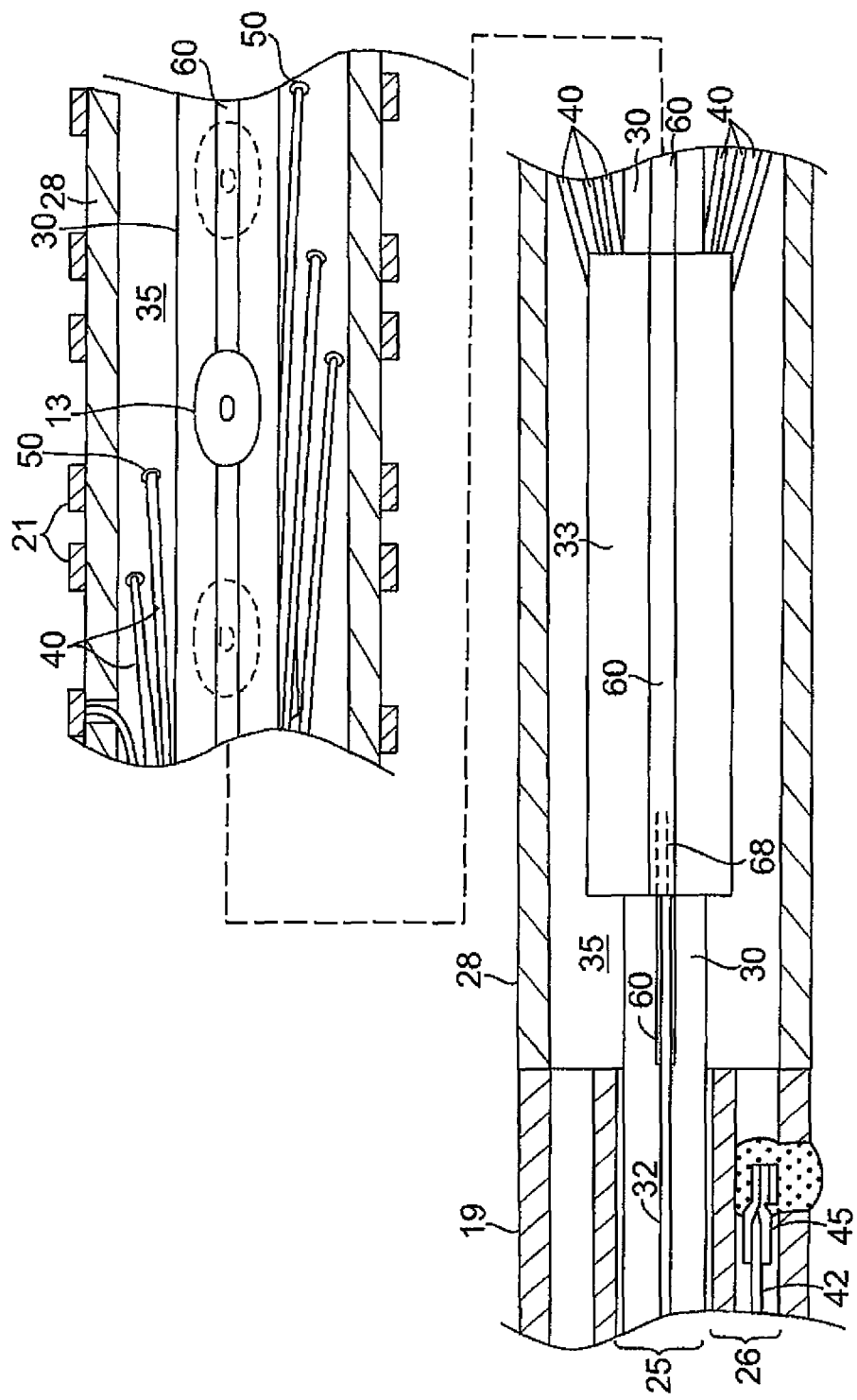
FIG. 3 is a top cross-sectional view of a distal tip section, in accordance with an embodiment of the present invention.

The puller wire 42 is anchored at its proximal end to the control handle 16 and anchored at its distal end at or near a distal end of the intermediate deflectable section 14 by means of a T-bar 45 (FIG. 3). The puller wire 42 is made of any suitable metal, such as stainless steel or Nitinol, and is coated with Teflon® or the like. The coating imparts lubricity to the puller wire 42. The compression coil 44 extends from the proximal end of the catheter body 12 to the proximal end of the tip section 14. The compression coil 44 is made of any suitable metal, such as stainless steel. The compression coil 44 is tightly wound on itself to provide flexibility, i.e., bending, but to resist compression. The inner diameter of the compression coil 44 is slightly larger than the diameter of the puller wire 42. The Teflon® coating on the puller wire 42 allows it to slide freely within the compression coil 44. Along its length, the outer surface of the compression coil 44 is covered by a flexible, non-conductive sheath 26 to prevent contact between the compression coil 44 and other components in the lumen 18. The sheath 26 may be made of polyimide.

Figure 12A:
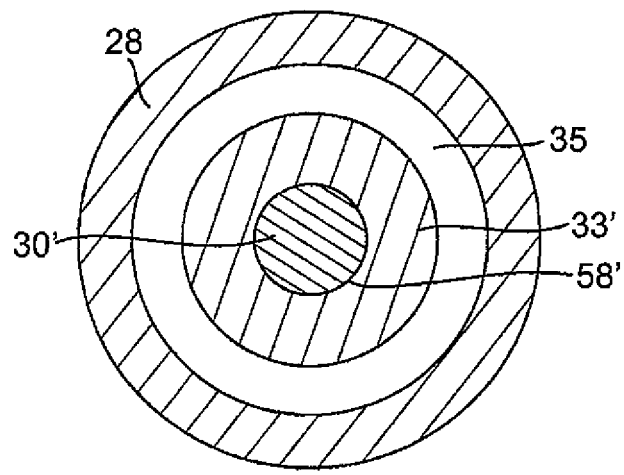
FIG. 12A is an end cross-sectional view of the distal tip section of FIG. 12, taken along line A-A.
Figure 12C:
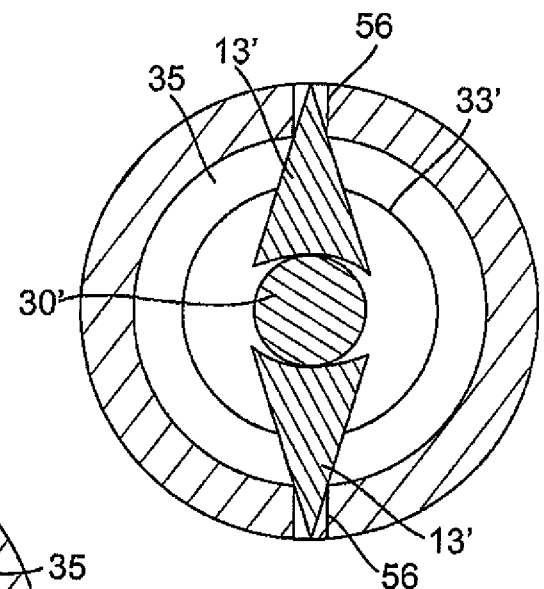
FIG. 12C is an end cross-sectional view of the distal tip section of FIG. 12, taken along line C-C.
Figure 12B:
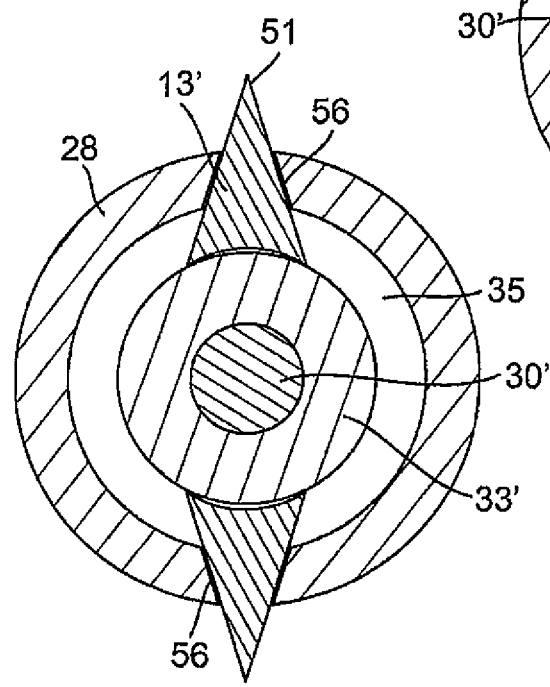
FIG. 12B is an end cross-sectional view of the distal tip section of FIG. 12, taken along line B-B.

The elongated support member 30 has a proximal end anchored in the control handle 16. It extends distally through the central lumen 18 of the catheter body 12, the center lumen 25 in the intermediate deflectable section 14 and further distally into the distal tip section 15 along a longitudinal center axis. The support member 30 may have any suitable cross-section, for example, circular (FIGS. 12A-12C), oval, polygonal, or rectangular (FIGS. 4A and 4B). It serves multiple functions, including, providing support for the needles 13 extending radially in the distal section 15, and a needle actuator 33 slidably mounted on the support member 30, and providing a 2-D (e.g., serpentine) or 3-D (e.g., helical) shape to the distal section 15. The support member 30 may be constructed of any suitable material having shape memory, including nitinol.

With reference to FIG. 3, the distal tip section 15 includes a short section of tubing 28 that extends from a distal end of the intermediate deflectable section 14. The tubing 28 has a single lumen 35 through which the support member 30 extends. Mounted on an outer surface of tubing 28 are ring electrodes 21, each of which has a respective lead wire 40 that extends through the lumen 35, the lumen 29 in the intermediate deflectable section 14 and the lumen 18 of the catheter body 12. One method for attaching a lead wire 40 to a ring electrode 21 involves first making a small hole 30 (see FIG. 3) in and through a side wall of the tubing 20. Such a hole can be created, for example, by laser drilling of the tubing or inserting a needle through the tubing 28 and heating the needle sufficiently to form a permanent hole 50. The lead wire 40 is then drawn through the hole by using a microhook or the like. The end of the lead wire 40 is then stripped of any coating and welded to the underside of the ring electrode 21, which is then slid into position over the hole and fixed in place with polyurethane glue or the like. Alternatively, each ring electrode 21 may be formed by wrapping the lead wire 40 around the outer surface of tubing 28 a number of times and stripping the lead wire of its own non-conductive coating on its outwardly facing surfaces. In such an instance, the lead wire 40 functions as a ring electrode. The plurality of ring electrodes ranges between about 6 to 12, and more preferably about 8 to 10. In the illustrated embodiment, the ring electrodes 21 are configured to function as bi-polar electrodes with each pair being situated proximal and distal of a respective needle 13.

The tubing 28 takes on any shape imparted by the support member 30, for example, a 2-D serpentine shape or a 3-D helical shape, so that the needles 13 and ring electrodes 21 can contact inner circumferential surface 53 of vessel 54 (see FIG. 1). A distal end of the tubing 28 has a dome plug 57 which seals the lumen 35 and anchors a distal end 30D of the support member 30. The dome plug 57 may comprise glue or adhesive, e.g., epoxy.

Figure 4:
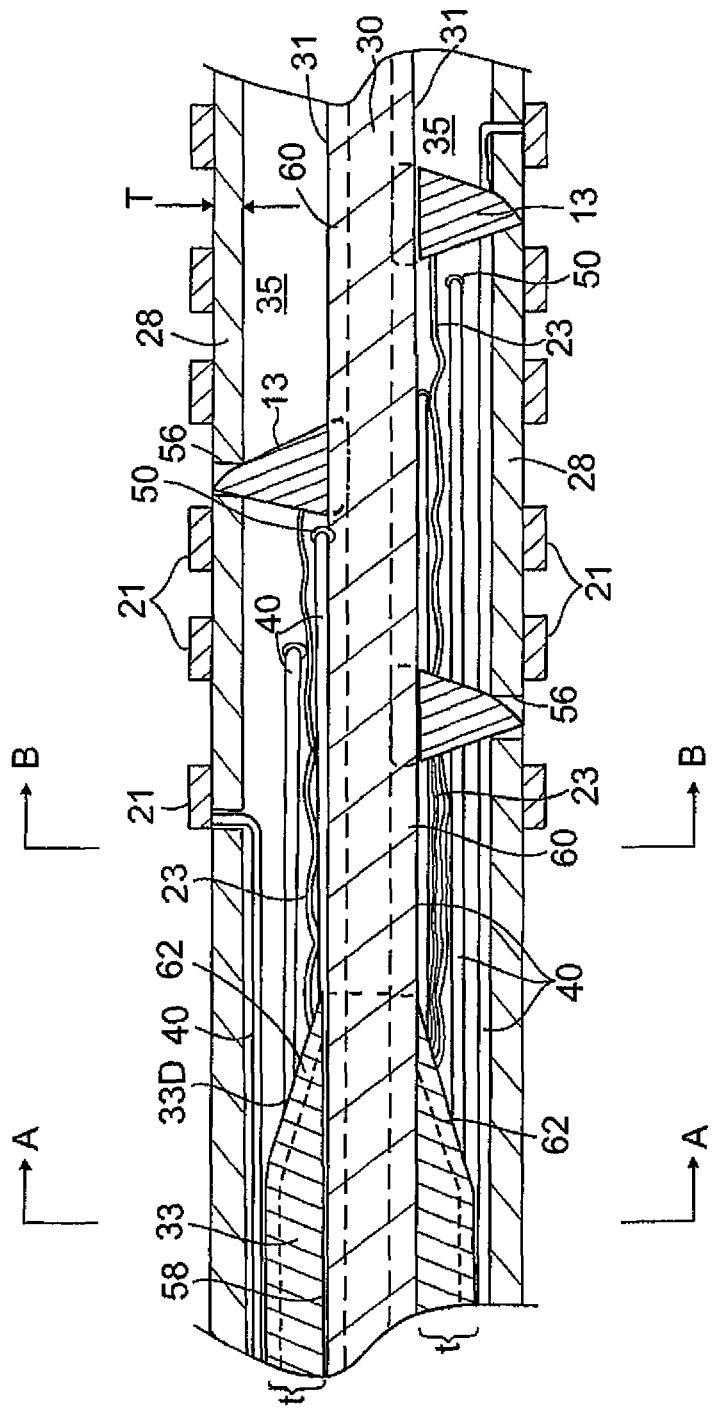
FIG. 4 is a side cross-sectional view of a distal tip section, in accordance with an embodiment of the present invention, with needles in a retracted position.
Figure 4C:
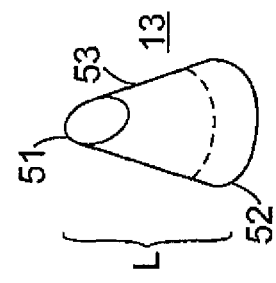
FIG. 4C is a perspective view of a needle.
Figure 4A:
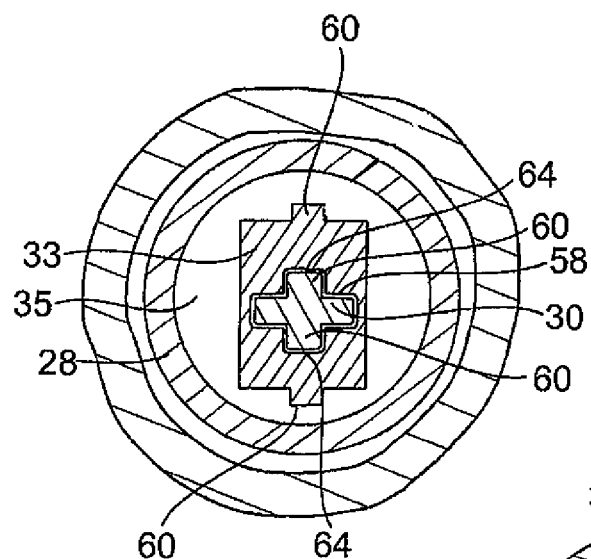
FIG. 4A is an end cross-sectional view of the distal tip section of FIG. 4, taken along line A-A.
Figure 4B:
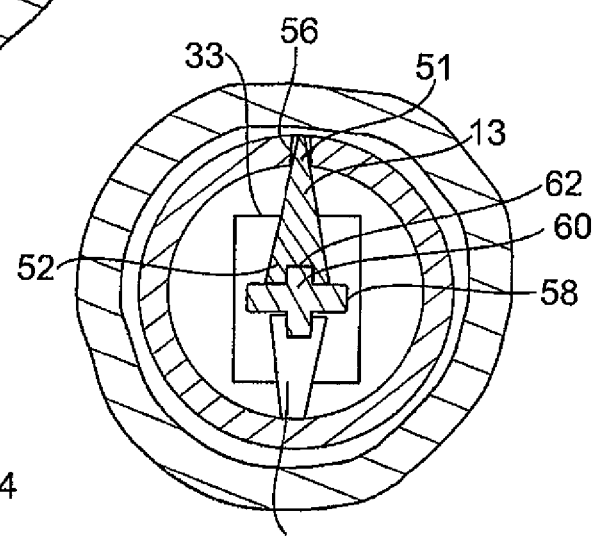
FIG. 4B is an end cross-sectional view of the distal tip section of FIG. 4, taken along line B-B.
Figure 5A:
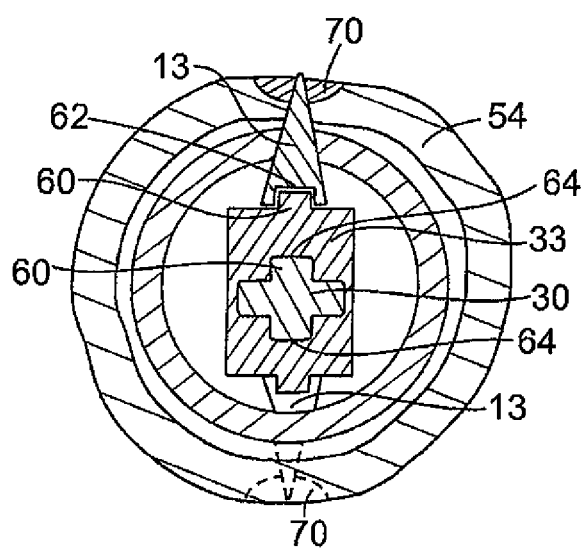
FIG. 5A is an end cross-sectional view of the distal tip section of FIG. 5, taken along line A-A.

As shown in FIGS. 3-5, each needle 13 has a generally oval cross-section with a conical shape providing a tapered profile, such that its base 52 is wider/larger than upper treatment (tissue contact) portion 53 and tip 51. The tip 51 is adapted to pierce and penetrate tissue layers of the vessel 54. The larger base 52 provides stability in enabling the needle 13 to rest against a radial outer surface 31 of the needle. In that regard, length L of the needle (see FIG. 4C) is greater than thickness T of the side wall of the tubing 28 so that the needle when deployed is long enough to extend radially outside of the tubing 28 and penetrate the tissue layers.

The needles 13 may be arranged for deployment in a variety of patterns. For example, the needles may be spaced uniformly or nonuniformly apart from each other, the needles may extend in multiple radial directions (instead of only 0 and 180 degrees as illustrated). In the illustrated embodiment, the needles 13 are spaced equi-distance apart and rest on opposing surfaces 31 of the support member 30 forming opposing rows. The needles may be staggered between the different rows. It may be preferable to arrange the needles so that ablation is conducted in locations that avoid forming a closed circumferential loop in the vessel so as to avoid stenosis. The plurality of needles may range between about 2 and 10, preferably about 4 and 8 and more preferably about six.

Each tip 51 is nested in a respective opening 56 formed in the side wall of the tubing 28, through which the treatment portion 53 (with the tip 51) of the needle passes to reach outside of the tubing 28. To that end, various parameters including the size of the opening, the thickness T of the tubing side wall and the elasticity of the tubing construction material are selected to allow expansion of the openings for the treatment portions 53 to pass through when the needles 13 are deployed, and ejection of the treatment portions 53 back into the lumen 35 to retract the needles.

To deploy the needles, the needle actuator 33 slidably mounted on the support member 30 is advanced distally to engage the needles and push them outwardly from the support member. In the illustrated embodiment, the needle actuator 33 is longitudinally aligned with the support member 30 and in a surrounding circumferential relationship therewith, with a center longitudinal passage 58 (FIG. 4A) through the support member 30 extends. The actuator 33 has a thickness t between the center passage and its outer surface which is predetermined so as to push the needle sufficiently outwardly out of the opening 56. However, if lead wires 40 are present, the thickness t should allow clearance for the lead wires 40 between the actuator 33 and an inner circumferential surface of the tubing 28.

A distal end 33D is tapered to facilitate engagement with the needles as the needle actuator 33 is advanced distally. As shown in FIG. 5B, a proximal side of each needle 13 has an angled base portion 52P (e.g., a shorter proximal length Lp from tip 51 to base 52 and a longer distal length Ld from tip 51 to base) whose angle generally corresponds with the tapered end 33D of the actuator 33. As the tapered end 33D encounters the needle 13, the tapered end 33 slides under the angled base portion 52P and helps lift the needle onto the tapered end. As the actuator 33 is further advanced distally, the needle 13 held by the opening 56 rides up the tapered end toward the proximal end 33P of the actuator 33 as the needle also protrudes outwardly through the opening 56 to engage tissue layers of the vessel 54.

As shown in FIGS. 3-5, to stabilize the needles' position and movement on the support member 30 and the actuator 33, a longitudinal track 60 is provided on the outer surface of the support member 30 and the actuator 33. In the illustrated embodiment, the track 60 is a raised ridge that extends along the length of the actuator 33 and the portion of the support member 30 within the tubing 28 of the distal tip section 15. A bottom contact surface of the base 52 of each needle 13 has a corresponding longitudinal recess 62 (FIGS. 4A-4C) that receives the track 60. The center passage 58 of the actuator 33 also has a corresponding longitudinal recess 64 that receives the track 60. As such, the needles 13 remains in alignment with the openings 56 whether they are supported on the support member 30 or the actuator 33, and the actuator 33 remains in alignment with the support member 30.

To control movement of the actuator 33, the advancing wire 32 is afforded longitudinal movement relative to the catheter 10. A proximal end of the wire 32 extends into the control handle and is manipulated via the control handle as described further below. The wire extends through the central lumen 18 (FIG. 2A) of the catheter body 12, the center lumen 25 (FIG. 2C) of the intermediate deflectable section 14, and the lumen 28 (FIG. 3) of the distal tip section 15. A distal end of the wire is anchored in a blind hole 68 (FIG. 3) formed in a proximal end of the actuator 33. To deploy the needles, the wire 32 is advanced distally which distally advances the actuator 33 on the support member 30. As described above, the tapered distal end 33D of the actuator 33 engages a needle and lifts the needle by the angled base 52P. As the actuator 33 continues to be distally advanced, the needle 13 held by the opening 56 rides up the tapered end 33D as the needle is pushed outwardly through the opening 56 by the outer surface of the actuator 33. In that regard, the force of the actuator acting on the needle exceeds the resistive elastic force of openings 56 of the tubing 28 against expansion. By selectively advancing the actuator 33 via the control handle 16, an operator can control which needles 13 are deployed. For example, the actuator 33 as shown in FIG. 5 has deployed the proximal-most needle and engaged the next needle in preparation for deployment. The distal-most needle would not be deployed unless the actuator 33 is further distally advanced to engage and lift it.

Retraction of the needles is accomplished by the operator proximally withdrawing the wire 32 via the control handle 16. As the actuator 33 moves proximally and the needles slide down the tapered end 33D, the needles held by the openings 56 are ejected inwardly by the resistive elastic force of the tubing 28 against expansion. The conical shape and tapered profile of the needles facilitate the ejection and thus the retraction of the needles back into the lumen 35. As the actuator 33 continues to be drawn proximally, the needles return to rest on the support member 30 and guided by the track 60 thereon.

The catheter 10 may include a tensile member, e.g., safety wire 23 (FIG. 4), that tethers a respective needle 113 to the actuator 33 as an extra safety feature to ensure that the needles are retracted with proximal movement of the actuator if they snag onto the tissue layers of the vessel. Each distal end of the safety wire 23 is anchored in a respective needle 13. The proximal ends of the safety wire 23 may be anchored to any portion of the actuator 33, for example, the tapered end 33D.

With the needles retracted, the catheter can be safely repositioned or moved in the vessel or removed from the patient's body. With the needles deployed, the tips 51 advantageously reach the outer tissue layers of the vessel. By using an electrically conductive wire 32, ablation energy can be transmitted along the catheter from an energy source proximal of the control handle 16 to the needle actuator 33 which in turn energizes only those needles 13 it engages to ablate and create lesions 70 (FIG. 5A) in the tissue layers of the vessel 54

Figure 6:
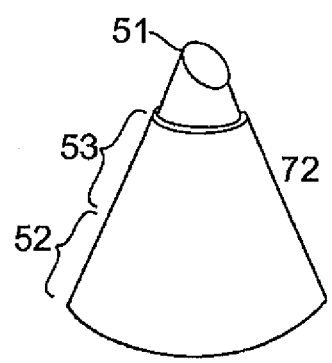
FIG. 6 is a perspective view of needle with a masked portion, in accordance with one embodiment of the present invention.

In an alternate embodiment, portion(s) of a needle 13 may be masked by a nonconductive coating, outer layer or sleeve 72, as illustrated in FIG. 6, for ablation of selective portion(s) or depth(s) of tissue layers of the vessel. For example, the base portion 52 and the treatment portion 53, with the exception of the tip 51 which remains exposed, may be masked so that energization of the needle results in ablation of solely the outer most tissue layers while sparing the mid and inner tissue layers. The coating 72 may be made of polyurethane or polyimide.

The lead wires 40 extend through the lumen 29 of tip section 14, the lumen 18 of the catheter body 12, the control handle 16, and terminate at their proximal ends in an input jack (not shown) that may be plugged into an appropriate monitor (not shown). If desired, the portion of the lead wires 40 extending through the catheter body 12, control handle 16 and proximal end of the tip section 14 may be enclosed or bundled within a protective tube or sheath.

In another alternate embodiment, a support member 30' and a needle actuator 33' each have a round cross-section, as shown in FIGS. 12 and 12A-12C. The needle actuator 33' has a lumen 58' through which the support member 30' extends. The outer diameter of the actuator 33' is greater than the outer diameter of the support member 30'. Accordingly, the curved base member 52 of needle 13', as shown in FIG. 12D, conforms to the greater outer diameter of the actuator 33' which notably does not prevent the needle 13' from resting on the support member 30' when in the retracted position. The proximal base 52P of the needle 13' is angled (e.g., with a shorter Lp and a longer Ld) to facilitate engagement with the distal end 33D' of the actuator 33' for lifting the needle 13' onto the actuator. In this embodiment, the needles 13' can be energized for ablation via the actuator 33'.

Temperature sensing means may be provided in the distal tip section for the ring electrodes and/or the needles, as understood by one of ordinary skill in the art. Any conventional temperature sensing means, e.g., a thermocouple or thermistor, may be used. A temperature sensing means for the tip electrode 36 comprises a thermocouple formed by an enameled wire pair. One wire of the wire pair is a copper wire, e.g., a number 40 copper wire which acts not only as part of the thermocouple, but as the electrode lead. The other wire of the wire pair is a construction wire, e.g., a number 40 construction wire, which gives support and strength to the wire pair. The wires and of the wire pair are electrically isolated from each other except at their distal ends where they contact and are welded or soldered. The wires may extend through the lumen carrying lead wires in the section 14 and through the central lumen 18 of the catheter body 12 into the control handle 16.

In the illustrated embodiments, an electromagnetic sensor 34 is contained within the lumen 27 at or near the distal end of the intermediate deflectable section 14. The electromagnetic sensor 34 is connected by means of electromagnetic sensor cable 36, which extends through the lumen 27 of the intermediate deflectable section 14, the lumen 18 of the catheter body 12 and into the control handle 16. The electromagnetic sensor cable 36 comprises multiple wires encased within a plastic covered sheath.

Figure 7:
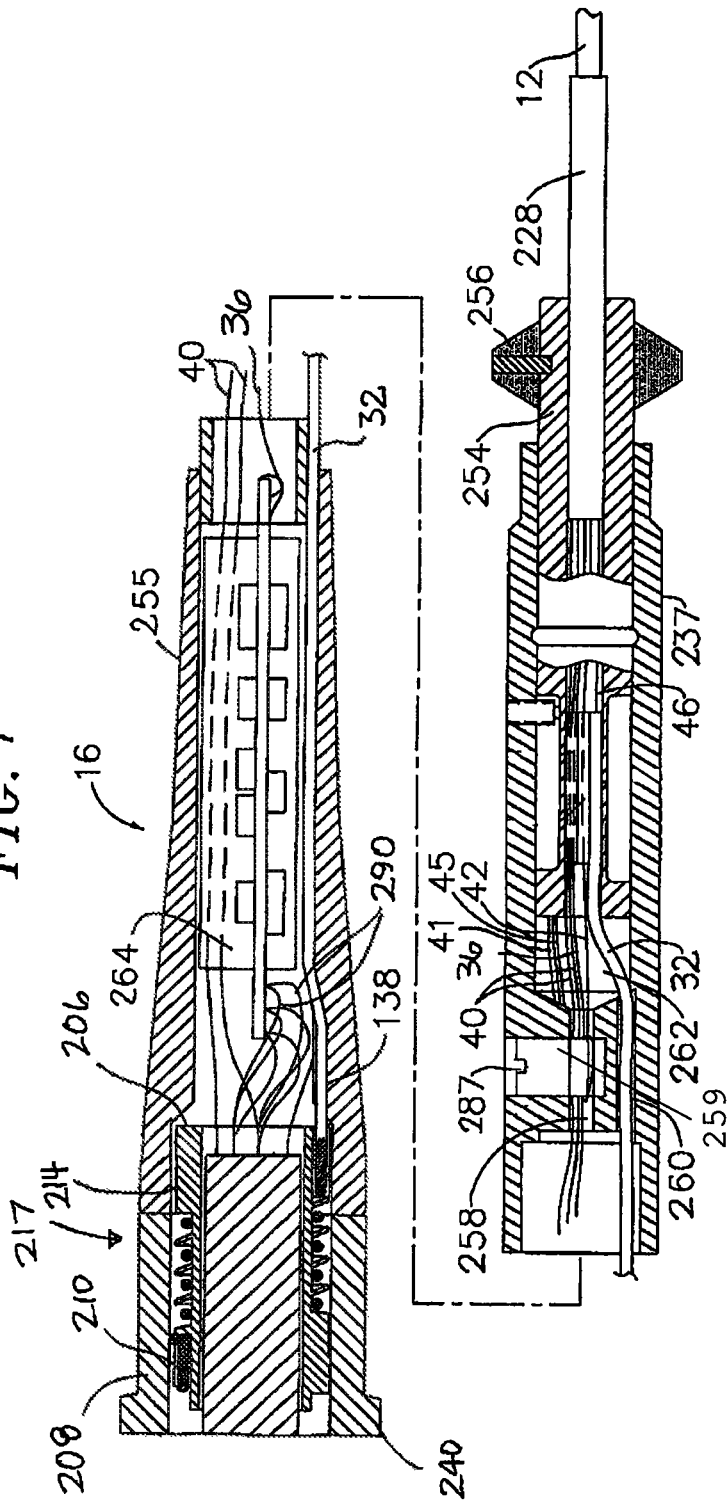
FIG. 7 is a side cross-sectional view of a control handle, in accordance with an embodiment of the present invention.

As shown in FIG. 7, the wires of the sensor cable 36 are connected to a circuit board 264 in the control handle 16. The circuit board 164 amplifies the signal received from the electromagnetic sensor and transmits it to a computer in a form understandable by the computer. A suitable electromagnetic sensor is described, for example, in U.S. Pat. No. 4,391,199, which is incorporated herein by reference. An electromagnetic mapping sensor 34 is manufactured by Biosense Ltd. Israel and marketed under the trade designation NOGA.

The electrode lead wires, thermocouple wires, electromagnetic sensor cable 36 and any other components or device may be allowed longitudinal movement within the catheter body 12 so they do not break when the catheter is deflected. Moreover, the advancing wire 32 can be advanced and retracted in accordance with a feature of the present invention. To provide for such lengthwise movement, there are tunnels provided through any and all glue joint(s) in the catheter body 12. The tunnels are formed by transfer tubes (not shown), made of short segments of polyimide tubing in one embodiment.

Longitudinal movement of the puller wire 42 relative to the catheter body 12 and the section 14, which results in deflection, is accomplished by suitable manipulation of the control handle 16. As shown in FIG. 7, the distal end of the control handle 16 comprises a piston 254 with a thumb control 256 for manipulating the puller wire 42. The proximal end of the catheter body 12 is connected to the piston 254 by means of a shrink sleeve 228.

The puller wire 42, lead wires 40, advancing wire 32 and electromagnetic sensor cable 36 extend through the piston 254. The piston 254 lies within a barrel 237 of the control handle. The barrel 237 is generally solid having a piston chamber for receiving the piston 254. Extending proximally from the piston chamber are two longitudinal tunnels 258 and 260 and a transverse hole 259 for receiving anchor pin 287. The first longitudinal tunnel 258 is in communication with the transverse hole 259. The lead wires 40 and sensor cable 36 extend through the first tunnel 258. The puller wire 42 also extends through the first tunnel 258 and is anchored to the anchor pin 287 in the transverse hole 259. The advancing wire 32 extends through the second tunnel 260. Between the distal end of the tunnels 258 and 260 and the proximal end of the piston 254, chamber 262 provides additional space to avoid undesirable bending of the components extending therethrough. The sensor cable 36 connects to the circuit board 264 in the control handle 16. Wires 290 connect the circuit board 264 to a computer and imaging monitor (not shown).

The advancing wire 32 extends through the control handle 16 and catheter body 12 and into the lumen 25 of the tubing 19 of the section 14. In accordance with a feature of the present invention, the wire 32 can be moved distally and proximally within catheter body by manipulation of the control handle 16, as discussed further below.

Figure 8:
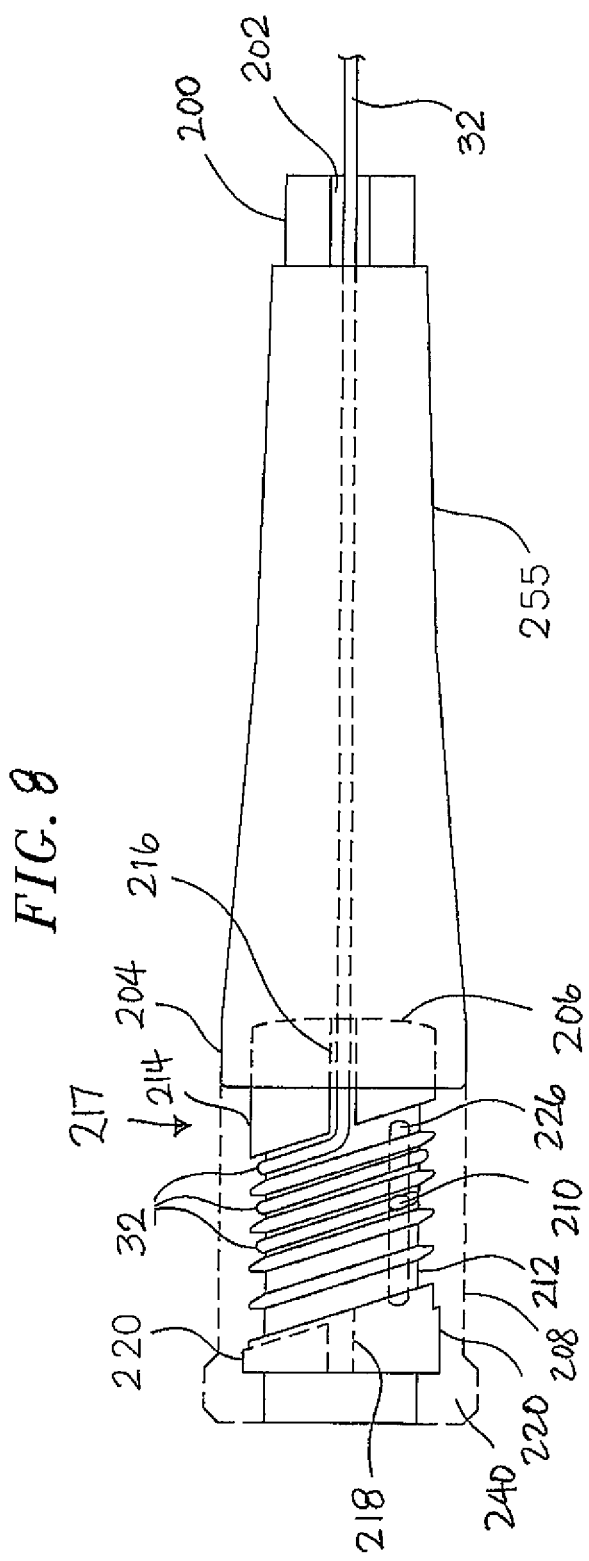
FIG. 8 is a top view of a control handle, in accordance with an embodiment of the present invention.
Figure 9A:
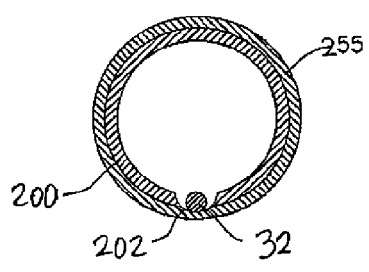
FIG. 9A is a longitudinal cross-sectional view of the barrel of FIG. 9, taken along line a-a.
Figure 9B:
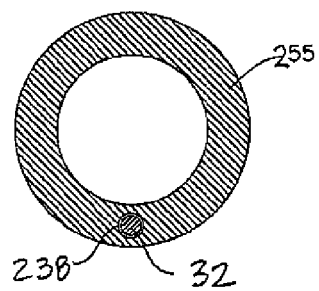
FIG. 9B is a longitudinal cross-sectional view of the barrel of FIG. 9, taken along line b-b.
Figure 9C:
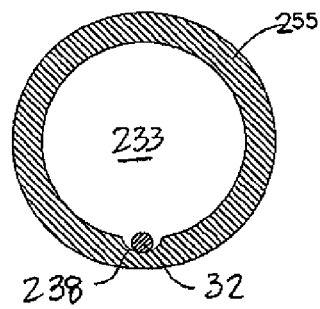
FIG. 9C is a longitudinal cross-sectional view of the barrel of FIG. 9, taken along line c-c.
Figure 9D:
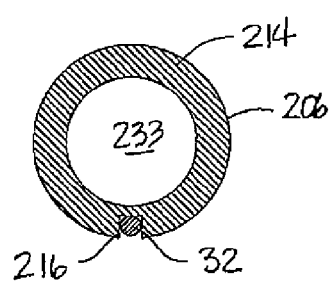
FIG. 9D is a longitudinal cross-sectional view of a threaded member of FIG. 9, taken along line d-d.
Figure 9E:
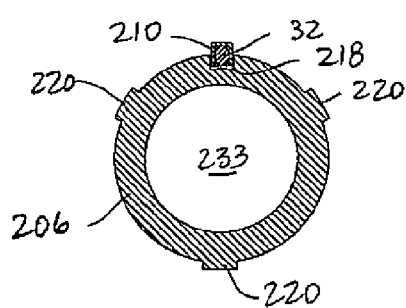
FIG. 9E is a longitudinal cross-sectional view of the threaded member of FIG. 9, taken along line e-e.
Figure 9F:
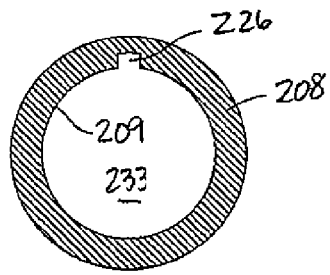
FIG. 9F is a longitudinal cross-sectional view of an adjustment member of FIG. 9, taken along line f-f.
Figure 9G:
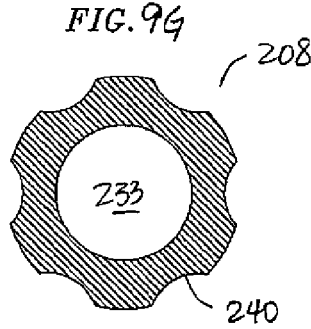
FIG. 9G is a longitudinal cross-section view of the adjustment member of FIG. 9, taken along line g-g.

In the illustrated embodiment of FIGS. 7-9, the control handle 16 has a second barrel 255 proximal the barrel 257 for an extended control handle configuration. The wire 32 extends proximally into the control handle through the piston 254 in the distal barrel 257, and through a distal end 200 of the proximal barrel 255 which has an opening or notch 202 in its general circular cross section (FIG. 9) to accommodate the wire 32. In the illustrated embodiment, a wire movement control mechanism 217, as means for allowing the advancement and retraction of the wire 32, is mounted on a proximal end 204 of the proximal barrel 255.

In the illustrated embodiment, the mechanism 217 includes a generally cylindrical threaded guide member 206, a generally cylindrical adjustment member 208 mounted thereon, and a guided member 210 (e.g., a slug or pin) situated between an outer surface 214 of the member 206 and an inner surface 209 of the member 208. The guided member slides in a helical guide channel 212, with a generally straight distal portion 216 and a generally straight proximal portion 218, all formed on the outer surface 214 of the guide member 206. In the illustrated embodiment, the helical guide channel 212 winds about the guide member 206 for approx. 4½ turns, such that the distal channel portions 216 and 218 are generally diametrical of each other (see FIGS. 9d and 9e).

The generally cylindrical adjustment member 208 is sized such that its interior is in close conformity with the member 206 to receive the latter in an overlapping, generally co-axial configuration. In that regard, the guide member 206 has protrusions 220 that lock with a recessed ring 222 formed in the inner surface 209 of the proximal end of the adjustment member 208, for a snap-fit coupling. Radial alignment for proper assembly of the advancement mechanism is accomplished when an elongated slot 226 formed in the inner surface 209 of the distal end of the member 208 receives the guided member 210 situated in the channel 212 of the member 206. As better illustrated in FIG. 8, the width of the slot is in close conformity to the width of the guided member 210 so that rotation of the adjustment member 208 (shown in broken lines) effectively moves the guided member 210 in the channel 212 of the guide member 206. Anchored to the guided member 210 is the proximal end of the wire 23, the adjacent distal portion of which is wound about the guide member 206 in the guide channel 212 and extends into the interior of the barrel 255 from the generally straight distal channel portion 216 on the member 206.

As shown in FIG. 9, the distal end of the guide member 206 is inserted into an enlarged conforming opening 230 at the proximal end of the barrel 255 which has a generally cylindrical hollow interior 232. With coupling of the members 208 and 206, the mechanism 217 forms a passage 233 that communicates with interior 232 of the barrel 255 and allows components, such as the lead wires 40 and the sensor cable 36 extending proximally through the control handle to pass through the barrel 255. While these components extend through the interior 232 of the barrel 255, the wire 32 extends through similarly except toward the proximal end of the barrel 255 which is provided with a passage 238 dedicated to the wire 32. Advantageously, the passage 238 is configured for alignment with the generally straight distal guide channel 216 of the guide member 206, so that the wire 32 can extend from the interior 232, through the passage 238 and be wound onto the member 206.

To assemble the mechanism 217 on the control handle, the guided member 210 with the proximal end of the wire 32 anchored thereto is placed in the channel 212 with the adjacent distal portion of the wire 32 wounded in the channels 212 and 216 distally therefrom. The distal end of the member 206 is inserted into the barrel 255. The member 208 is inserted distally over the member 206, with the slot 226 aligned with the guided member 210, until the protrusions 220 of the member 206 lock in the ring recess 222 of the member 208 and the distal end of the member 208 generally abuts with the proximal end of the barrel 255.

In operation to accomplish the advancement and retraction of the wire 32 for deploying and retracting the needles 13 in the distal tip section 15, the mechanism 217 can be manipulated by the user through rotation of the adjustment member 208 by means of a knob 240 formed on an outer surface at the proximal end of the member 208. As the user rotates the knob (e.g. clockwise in the illustrated embodiment), the slot 226 on the inner surface 209 is rotated about the longitudinal axis of the member 208 to drive the guided member 210 helically along the guide channel 212 in the distal direction, which in turn distally pushes the wire 32 connected to the guided member 210. Such advancement can continue until the guided member 210 reaches the generally straight distal guide channel 216, at which location the distal end of the slot 226 blocks further distal movement of the guided member 210.

To withdraw the wire 32 and retract the needles 13, the user rotates the knob 240 in the opposite direction (e.g., counterclockwise in the illustrated embodiment) which causes the slot 226 to drive the guided member 210 helically in the proximal direction, which in turn draws the wire 32 proximally. This retraction can continue until the guided member 210 reaches the generally straight proximal guide channel 216, at which location the proximal end of the slot 226 prevents further proximal movement of the guided member 210.

It is understood by one of ordinary skill in the art that an overlapping longitudinal region between the slot 226 and the helical guide channel 212 defines the possible travel distance of the guided member 210 and thus the advancement/retraction distance of the wire 32, and therefore variations in either or both of the length of the slot and the longitudinal spread of the channel 212 as between channels 216 and 218, and/or the degree of overlap can alter the travel distance of the guided member 210 and the maximum advancement/retraction distance of the wire 32. It is further understood that other variations, including a change in the diameter of the guiding member 206 (which changes the circumference of the helical channel 212 and the maximum advancement/retraction distance) and/or the number of windings or turns of the helical channel can also alter the travel distance and maximum advancement/retraction distance.

Figure 10:
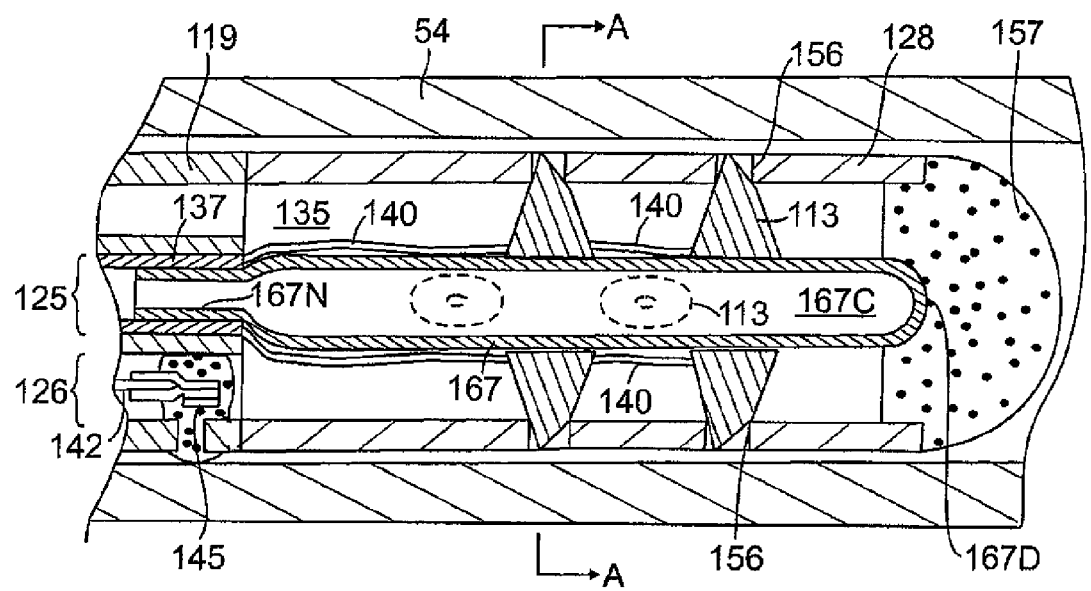
FIG. 10 is a side cross-sectional view of a distal tip section, in accordance with another embodiment of the present invention, with needles in a retracted position.
Figure 11:
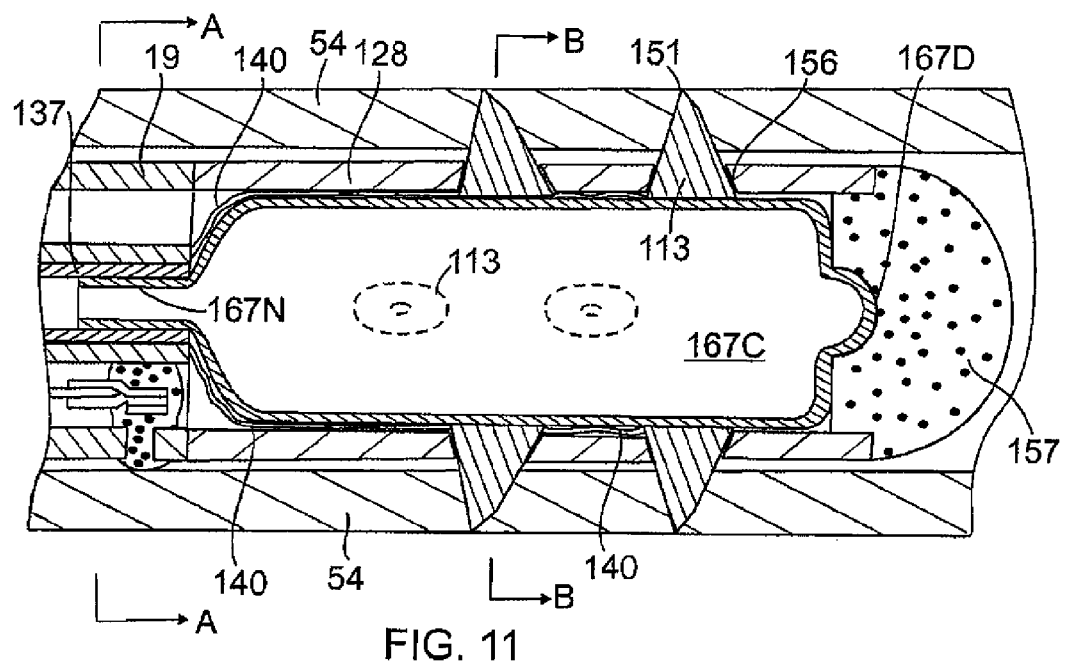
FIG. 11 is a side cross-sectional view of the distal tip section of FIG. 10, with needles in a deployed position.

In another alternative embodiment of the present invention, a catheter 100 is illustrated in FIGS. 10 and 11. The catheter 100 has similarities and differences compared to the catheter 10, some of which are discussed below. Similar components and structures are identified with similar reference numerals.

The catheter 100 includes a catheter body 112 and a distal tip section 115. Like the catheter 10, the catheter 110 may also include an intermediate deflectable section 114 if deflection is desired. As shown in FIG. 11A, tubing 119 of the intermediate deflectable section 114 has multiple lumens, for example, a center lumen 125 for a fluid tubing 137, an off-axis lumen 126 for puller wire 142, lumen 135 for lead wires 140, and lumen 127 for em sensor 134 and sensor cable 136. Each of these components extends through the catheter body 112 before entering their respective lumen in the intermediate deflectable section 14.

The distal tip section 115 has a single-lumened tubing 128 with lumen 135 which is occupied by an elongated balloon member 167 with an interior cavity 167C, a proximal neck inlet portion 167N and a distal tip 157D. The inlet portion 167N is received in a distal end of the fluid tubing 137 at or near the distal end of the tubing 119. The distal tip 167 is anchored in a dome plug 157 which also seals the lumen 135. Accordingly, the balloon member extends along a longitudinal center axis of the distal tip section 115.

Needles 113 are affixed by a bottom surface of their base 152 to an outer circumferential surface of the balloon member 167 by adhesives so the needles extend outwardly in a radial direction. When the balloon member is in a deflated state, the needles are retracted in the distal tip section 115 with their tips 151 nested in openings 156 formed in the tubing 128. When fluid is introduced in the fluid tubing 137 and delivered into the cavity 167C of the balloon member through the inlet portion 167N, the balloon member inflates and deploys the needles 113 to push through the openings 156 and extend radially outside of the tubing 128. As shown in FIG. 11B, the deployed needles pierce and penetrate tissue layers of the vessel 54. The needles are pushed through the openings 156 because radially outward force exerted by the inflated balloon member overcomes the resistive elastic force of the openings 156 of the tubing 128 against expansion. The needles 113 may also be selectively masked as described above (see FIG. 6) to ablate portions or different depth(s) of the tissue layers of the vessel 54. Moreover, the amount of fluid passed into the balloon member is adjustable so as to adjust the expansion of the balloon member in selecting the degree or depth of extension of the needles into the tissue layers.

To retract the needles 113, fluid is evacuated or drained from the balloon member 167 which deflates. In the absence or removal of the radially outward force, the needles 113 are ejected inwardly into the lumen 135 by the resistive elastic force of the openings 156 of the tubing 128 against expansion. Forceful evacuation of the fluid from the balloon member may also actively draw the needles back into the lumen 135. With the needles retracted, the catheter 100 may be repositioned or removed from the patient's body.

Suitable control handles are described in U.S. application Ser. No. 12/550,204, filed Aug. 28, 2009, Ser. No. 11/863,149, filed Sep. 27, 2007 and Ser. No. 12/550,307, filed Aug. 28, 2009, the entire contents of all of which are hereby incorporated by reference.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. For example, the advancing wire control mechanism may be integrated anywhere along the control handle. User interface may be modified to allow for a linear motion deflection knob rather than the rotational knob mentioned above. If bi-directional deflection is desired, a second puller wire may be provided, as understood by one of ordinary skill in the art. Moreover, the drawings are not necessarily to scale.

Accordingly, the foregoing description should not be read as pertaining only to the precise structures described and illustrated in the accompanying drawings, but rather should be read consistent with and as support to the following claims which are to have their fullest and fair scope

What is claimed is:

1. A catheter comprising:
    a catheter body;
    a distal tip section having:
        a tubing with a lumen, the tubing having at least one opening;
        at least one needle in the lumen configured to assume a deployed position and a retracted position;
        an elongated support member extending through at least the lumen of the distal tip section;
        an actuator extending through at least the lumen of the distal tip section and configured for longitudinal movement on and relative to the elongated support member,
    a control handle having a member adapted to control longitudinal movement of the actuator relative to the elongated support member; and
    a wire adapted for longitudinal movement relative to at least the catheter body for moving the actuator relative to the elongated support member;
    wherein the at least one needle is supported by the elongated support member while in the retracted position and the at least one needle is pushed outwardly in a radial direction by the actuator while in the deployed position.

2. The catheter of claim 1, wherein the at least one needle is generally within the distal tip section while in the retracted position and wherein the at least one needle has a treatment portion outside of the distal tip section through the at least one opening while in the deployed position.

3. The catheter of claim 2, wherein the treatment portion extends radially from the distal tip section through the at least one opening while the at least one needle is in the deployed position.

4. The catheter of claim 1, wherein the at least one needle is supported in a radial direction relative to the distal tip section in both the retracted position and the deployed position.

5. The catheter of claim 1, wherein the actuator is proximal of the at least one needle while the at least one needle is in the retracted position.

6. The catheter of claim 1, wherein at least a portion of the actuator is positioned between the at least one needle and the elongated support member while the at least one needle is in the deployed position.

7. The catheter of claim 1, wherein upon moving the actuator distally relative to the elongated support member the at least one needle moves from the retracted position to the deployed position.

8. The catheter of claim 1, wherein upon moving the actuator proximally relative to the elongated support member the at least one needle moves from the deployed position to the retracted position.

9. The catheter of claim 1, wherein the actuator has a tapered distal end to facilitate engagement with the at least one needle.

10. The catheter of claim 9, wherein the tapered distal end is configured to lift the at least one needle off the support member and guide the at least one needle onto the actuator.

11. The catheter of claim 9, wherein the at least one needle has an angled portion configured to engage with the tapered distal end.

12. The catheter of claim 1, wherein the distal tip section comprises a plurality of needles and the actuator is configured for adjustable longitudinal movement relative to the elongated support member in deploying selective ones of the plurality of needles.

13. The catheter of claim 1, wherein the elongated support member has a distal portion with a 2D or 3D shape.

* * * * *